US010080543B2

(12) United States Patent
Coimbatore Renukanandhan et al.

(10) Patent No.: US 10,080,543 B2
(45) Date of Patent: Sep. 25, 2018

(54) INTEGRATED MODULAR SYSTEM FOR MANAGING PLURALITY OF MEDICAL DEVICES

(71) Applicant: GENERAL ELECTRIC COMPANY, Schenectady, NY (US)

(72) Inventors: Satish Kumar Coimbatore Renukanandhan, Bangalore (IN); Mahendra Patil, Bangalore (IN); Narasimha Murthy Vinay, Bangalore (IN); Samarth Bhat, Bangalore (IN)

(73) Assignee: General Electric Company, Schenectady, NY (US)

( * ) Notice: Subject to any disclaimer, the term of this patent is extended or adjusted under 35 U.S.C. 154(b) by 345 days.

(21) Appl. No.: 14/955,852

(22) Filed: Dec. 1, 2015

(65) Prior Publication Data
US 2016/0228082 A1    Aug. 11, 2016

(30) Foreign Application Priority Data

Dec. 1, 2014   (IN) .............................. 6008/CHE2014

(51) Int. Cl.
| | | |
|---|---|---|
| *B62B 3/02* | (2006.01) | |
| *A61B 8/00* | (2006.01) | |
| *A61B 50/10* | (2016.01) | |
| *A61B 50/13* | (2016.01) | |
| *A61B 6/04* | (2006.01) | |
| *A61B 50/15* | (2016.01) | |

(52) U.S. Cl.
CPC ................ *A61B 8/00* (2013.01); *A61B 50/10* (2016.02); *A61B 50/13* (2016.02); *A61B 6/04* (2013.01); *A61B 50/15* (2016.02); *A61B 2050/105* (2016.02); *A61B 2505/05* (2013.01); *A61B 2560/0437* (2013.01); *A61B 2560/0443* (2013.01); *B62B 3/02* (2013.01)

(58) Field of Classification Search
CPC .. A61B 8/00; A61B 50/10; A61B 6/04; A61B 2560/0437; A61B 2560/0443; B62B 1/04; B62B 1/10; B62B 1/12; B62B 3/02
See application file for complete search history.

(56) References Cited

U.S. PATENT DOCUMENTS 3,090,381 A * 5/1963 Watson .............. A61G 13/0036
                                                  5/624
3,304,116 A * 2/1967 Stryker .................... A61G 7/00
                                                   296/20
(Continued)

*Primary Examiner* — Erez Gurari
(74) *Attorney, Agent, or Firm* — GE Global Patent Operation; Marc A. Vivenzio

(57) ABSTRACT

An integrated modular system for managing plurality of medical devices in an interventional procedure room and usable in conjunction with a patient positioner having an articulating tabletop is disclosed. The integrated modular system comprises a wheeled base; an upwardly extended support structure mounted on the wheeled base; two or more device integration modules removably mounted on the upwardly extended support structure; one or more coupling devices arranged in a linearly guided fashion with the upwardly extended support structure; wherein the one or more coupling devices couples the articulating tabletop of a patient positioner and the upwardly extended support structure.

20 Claims, 5 Drawing Sheets

(56) References Cited

U.S. PATENT DOCUMENTS

| | | | |
|---|---|---|---|
| 3,624,396 A * | 11/1971 | Watson | A61F 5/04 378/189 |
| 3,818,516 A * | 6/1974 | Hopper | A61B 6/04 378/198 |
| 4,905,266 A * | 2/1990 | Kuck | A61B 6/04 378/177 |
| 5,016,948 A * | 5/1991 | Welch | A61G 12/001 211/126.15 |
| 5,155,758 A * | 10/1992 | Vogl | A61B 6/04 378/208 |
| 5,380,034 A * | 1/1995 | Wilson | A61G 5/006 280/30 |
| 5,468,216 A * | 11/1995 | Johnson | A61H 1/0292 5/616 |
| 5,619,763 A * | 4/1997 | Randolph | A61B 6/04 37/209 |
| 5,658,315 A * | 8/1997 | Lamb | A61F 5/04 602/32 |
| 5,806,111 A * | 9/1998 | Heimbrock | A61G 1/0225 280/47.371 |
| 5,996,149 A * | 12/1999 | Heimbrock | A61B 6/04 378/177 |
| 6,266,831 B1 * | 7/2001 | Heimbrock | A61G 1/04 248/231.61 |
| 6,286,164 B1 * | 9/2001 | Lamb | A61G 13/0036 128/845 |
| 6,398,409 B1 * | 6/2002 | Brooks | A61B 6/04 378/189 |
| 6,971,997 B1 * | 12/2005 | Ryan | A61F 5/04 5/614 |
| 7,213,279 B2 * | 5/2007 | Weismiller | A61G 7/00 5/618 |
| 7,367,571 B1 * | 5/2008 | Nichols | B25H 1/12 280/47.131 |
| 7,412,311 B2 * | 8/2008 | Georgi | A61G 5/043 318/580 |
| 8,056,163 B2 * | 11/2011 | Lemire | A61G 7/001 5/610 |
| 8,474,835 B1 * | 7/2013 | Rossi | B62B 3/02 280/47.35 |
| 2003/0074735 A1 * | 4/2003 | Zachrisson | A61G 13/04 5/607 |
| 2004/0133979 A1 * | 7/2004 | Newkirk | A61G 13/0036 5/600 |
| 2005/0223491 A1 * | 10/2005 | McCrimmon | A47C 19/045 5/11 |
| 2006/0133580 A1 * | 6/2006 | Vezina | A61B 6/04 378/177 |
| 2007/0107122 A1 * | 5/2007 | Georgi | A61G 13/04 5/11 |
| 2007/0251011 A1 * | 11/2007 | Matta | A61B 19/0248 5/624 |
| 2009/0158523 A1 * | 6/2009 | Burak, Jr. | A61G 7/1019 5/87.1 |
| 2010/0172468 A1 * | 7/2010 | Gregerson | A61B 5/0555 378/20 |
| 2011/0174936 A1 * | 7/2011 | Cox | F16M 11/22 248/121 |
| 2012/0203377 A1 * | 8/2012 | Paydar | G01K 3/005 700/232 |
| 2012/0212116 A1 * | 8/2012 | McRorie | B62B 3/02 312/249.13 |
| 2013/0113171 A1 * | 5/2013 | Pennings | B62B 3/004 280/47.34 |
| 2013/0198958 A1 * | 8/2013 | Jackson | A61G 13/0036 5/607 |
| 2013/0247301 A1 * | 9/2013 | Daley | A61G 13/101 5/613 |
| 2015/0030135 A1 * | 1/2015 | Choi | A61B 6/4405 378/189 |
| 2015/0135441 A1 * | 5/2015 | Sommer | A61G 13/0036 5/613 |
| 2015/0223890 A1 * | 8/2015 | Miller | A61B 5/117 705/2 |
| 2016/0000627 A1 * | 1/2016 | Jackson | A61G 13/02 5/608 |
| 2017/0000675 A1 * | 1/2017 | Hight | A61B 6/04 |
| 2017/0156684 A1 * | 6/2017 | Van De Rijdt | A61B 6/04 |
| 2017/0304020 A1 * | 10/2017 | Ng | A61B 90/50 |

* cited by examiner

INTEGRATED MODULAR SYSTEM FOR MANAGING PLURALITY OF MEDICAL DEVICES

FIELD OF THE INVENTION

The subject matter disclosed herein relates to a system for managing plurality of medical devices in an integrated fashion within an interventional procedure rooms such as a radiology lab, catheterization lab, surgical/operating rooms etc. More specifically it relates to a system configured to be deployed alongside a patient positioner typically used in an interventional procedure room such as a radiology lab, catheterization lab, surgical/operating room etc.

BACKGROUND OF THE INVENTION

During interventional procedures such as electrophysiology, PCI or surgery, plurality of medical devices are likely to be used to assist in acquiring necessary clinical data (such as ultrasound images, ECG waveforms, heart rate, blood pressure, SPO2 or other vital signs) or to deliver specific energy for stimulation or ablation of tissues in a specific organ such as the heart or to gain intravenous access to internal anatomical structures for deploying implantable devices such as stents. Many of these medical devices have several cables, tubes, catheters or probes etc. that facilitate all necessary device-to-device or device-to-patient connections to establish a useful complete set-up for a given procedure. These devices are needed to be deployed in a close proximity with the patient positioner in order to manage with the limited length of cables, catheters, tubes & probes. Further in situations where the patient positioner has an articulating tabletop to facilitate longitudinal, lateral or rotational movements, there is a very high likelihood of some cables, catheters, tubes or probes to be pulled off or snapped during the articulation of the tabletop and resulting into unsafe conditions for the patient, the care givers or the devices. In absence of a proper system to manage plurality of medical devices and all associated cables, catheters, probes and tubes, enormity of messy cables is often encountered that pose several patient, staff and devices safety challenge including snapped cables, trip hazards and difficulties in cleaning or housekeeping inside the procedure room etc. The conventional systems also render poor flexibility in preparing or modifying the set-up as may be necessary from case to case and from time to time.

Accordingly, a need exists for an improved system to manage plurality of medical devices in an integrated fashion within an interventional procedure room such as a radiology lab, catheterization lab, surgical/operating room etc.

SUMMARY OF THE INVENTION

The object of the invention is to provide an improved system to manage plurality of medical devices in an integrated fashion within an interventional procedure room such as a radiology lab, catheterization lab, surgical/operating room etc., which overcomes one or more drawbacks of the prior art. This is achieved by an integrated modular system having the capability of housing and interconnecting a plurality of medical devices in an orderly manner as defined in the independent claim.

One advantage with the disclosed integrated modular system is that it provides an improved way of housing and interconnecting plurality of medical devices within a common platform—which can be easily moved close to the patient positioner or taken away to a parking location to efficiently deploy a useful configuration of medical devices on a case-to-case basis from time-to-time. Further all the cables, catheters, tubes or probes facilitating device-to-device and device-to-patient connections can be managed in an efficient and orderly manner to eliminate all associated hazards. The system allows all necessary articulations of the tabletop of a patient positioner that may be necessary in situations such as loading and unloading of the patient on the tabletop, panning the tabletop to gain access to a desired anatomical region of the patient's body or for positioning the patient with respect to an X-ray imaging gantry to acquire X-ray/fluoroscopic images or sequences.

In an embodiment an integrated modular system for managing a plurality of medical device in an interventional procedure rooms such as a radiology lab, catheterization lab, surgical/operating rooms is disclosed. The integrated modular system comprises a wheeled base and an upwardly extended support structure mounted on the wheeled base. Two or more device integration modules are removably mounted on the upwardly extended support structure. One or more coupling devices are arranged in a linearly guided fashion with the upwardly extended support structure. The one or more coupling devices couple an articulating table top of a patient positioner and the upwardly extended support structure.

In another embodiment a method of assembling an integrated modular system for managing a plurality of medical devices is disclosed. The method includes removably mounting an upwardly extended support structure on a wheeled base; removably mounting two or more device integration module on the upwardly extended support structure; and arranging one or more coupling devices in a linearly guided fashion with the support structure, wherein the one or more coupling devices couple an articulating table top of the patient positioner and the upwardly extended support structure.

A more complete understanding of the present invention, as well as further features and advantages thereof, will be obtained by reference to the following detailed description and drawings.

DETAILED DESCRIPTION OF THE INVENTION

Figure 1:
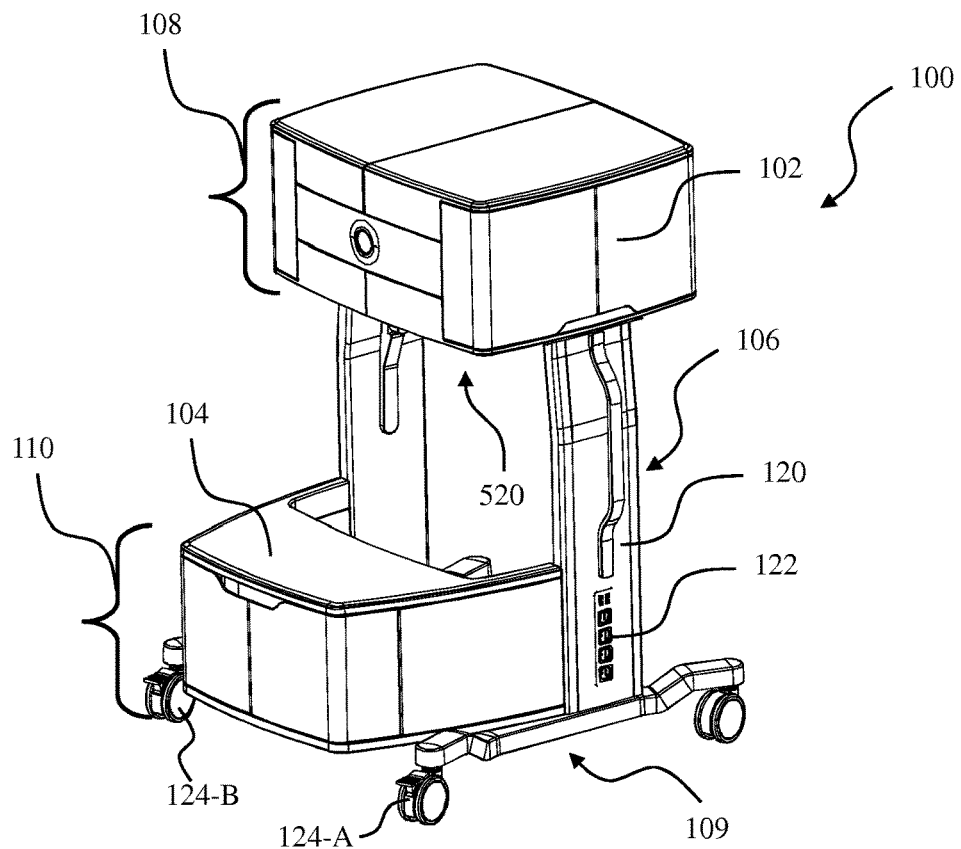
FIG. 1 is a schematic illustration of an integrated modular system for managing a plurality of medical devices in an interventional procedure room having two device integration modules disposed thereon according to an embodiment.

In the following detailed description, reference is made to the accompanying drawings that form a part hereof, and in which is shown by way of illustration specific embodiments that may be practiced. These embodiments are described in sufficient detail to enable those skilled in the art to practice the embodiments, and it is to be understood that other embodiments may be utilized and that logical, mechanical and other changes may be made without departing from the scope of the embodiments. The following detailed description is, therefore, not to be taken as limiting the scope of the invention.

As discussed in detail below, embodiments of an integrated modular system for managing plurality of medical devices in an interventional procedure room is disclosed. An integrated modular system for managing plurality of medical devices in an interventional procedure room and usable in conjunction with a patient positioner having an articulating tabletop is disclosed. The integrated modular system comprises a wheeled base; an upwardly extended support structure mounted on the wheeled base; two or more device integration modules removably mounted on the upwardly extended support structure; one or more coupling devices secured in a linearly guided fashion with the upwardly extended support structure; wherein the one or more coupling devices couples the articulating tabletop of a patient positioner and the upwardly extended support structure. The coupling device may be a mechanical interlocking device that serves as a means for preventing an unwarranted relative motion between the articulating tabletop and the plurality of medical devices housed within the device integration modules thereby averting possibilities of patient connected cables, catheters, tubes and probes being pulled off accidently and associated patient safety risks. The mechanical interlocking devices also enable quick disengagement of the integrated modular system from the patient positioner to help reposition it to a remote location to provide free peripheral access around the patient positioner to help during patient handling or during cleaning of procedure room floor. Further a network of cable raceways for navigating cables in a concealed fashion is integrated within the upward extended support structure to assist in overcoming the menace of cluttered cables while enabling efficient device-to-device and device-to-patient connectivity. This also enables connectivity between the plurality of devices deployed within the device integration modules to share power, data, and signals mutually or with other remotely situated external devices. Internal arrangement for sharing power, data and signal resources among the plurality of devices through a common bus or an array of connectors, plug and sockets etc. and hence eliminates the need for multiple power lines or data or signal cables to be fetched from floor or wall mounted sockets/ports and help eliminate enormity of cables over the floor and improves ease of cleaning inside a procedure room.

FIG. 1 is a schematic illustration of an integrated modular system 100 for a healthcare environment according to an embodiment. In a healthcare environment especially a hospital, an interventional procedure room, an operation theatre in the hospital and a diagnostic lab, multiple medical equipment may be placed and they may be connected to the patient using wires or cables and probes. The medical equipment may be ablation devices, signal amplifiers, mapping devices, patient monitoring devices and ultrasound devices. The equipment may be connected to each other or to other power units using multiple wires and thus the environment may look complex and cluttered due to entangling wires or cables. The cables or wires may include but not limited to electric power cables, data cables and pneumatic tubing. The integrated modular system 100 includes two or more device integration modules for instance a first device integration module 102 and a second device integration module 104 (hereinafter referred to as a device integration module 102 and a device integration module 104). The device integration modules 102 and 104 are mounted on an upwardly extended supporting structure 106. Each device integration module is modular in structure and arrangement as they are removably mounted. These device integration modules can be removed from the upwardly extended supporting structure 106 (hereinafter referred to as supporting structure 106). The integrated modular system 100 is also provided with a wheeled base 109 that enables it to move from one location to another.

Figure 2:
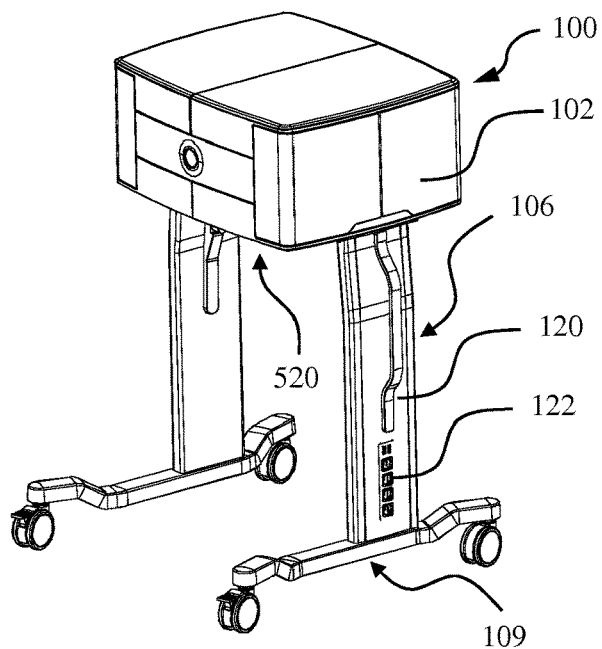
FIG. 2 is a schematic illustration of an integrated modular system for managing a plurality of medical device in an interventional procedure room according to an embodiment having one device integration module disposed thereon.

FIG. 2 illustrates the integrated modular system 100 with the device integration module 102 disposed thereon while the device integration module 104 is moved out. In an embodiment any device integration module of the integrated modular system such as the integrated modular segment 100 may have device integration modules that can be slided and disposed on a supporting structure. In this case the supporting structure may have sliding structures that facilitate the device integration modules to be slided and placed on the supporting structure. In another embodiment the device integration module can be snapped and disposed in the supporting structure. It may be envisioned that any other mechanism or arrangement may be present for mounting the device integration modules in the supporting structure without limiting from the scope of this disclosure.

Further in another embodiment multiple device integration modules of different shapes and sizes may be disposed on the supporting structure 106. As shown in FIG. 1, the device integration module 102 is positioned at a first region 108 of the supporting structure 106 and the device integration module 104 is positioned at a second region 110 of the supporting structure 106. In an embodiment location of the device integration module 102 and the device integration module 104 in the supporting structure 106 can be interchanged. In an embodiment the device integration module 102 and the device integration module 104 are disposed towards mutually opposite orientation as shown in FIG. 1. The change in position of the device integration modules can be done based on user preference. Thus the device integration module 102 and the device integration module 104 may be arranged in any other location and may be arranged with respect to each other in any other configuration or orientation or direction on the supporting structure 106. Moreover the integrated modular system 100 may include more than two device integration modules arranged in different configuration without limiting from the scope of this disclosure.

Figure 3:
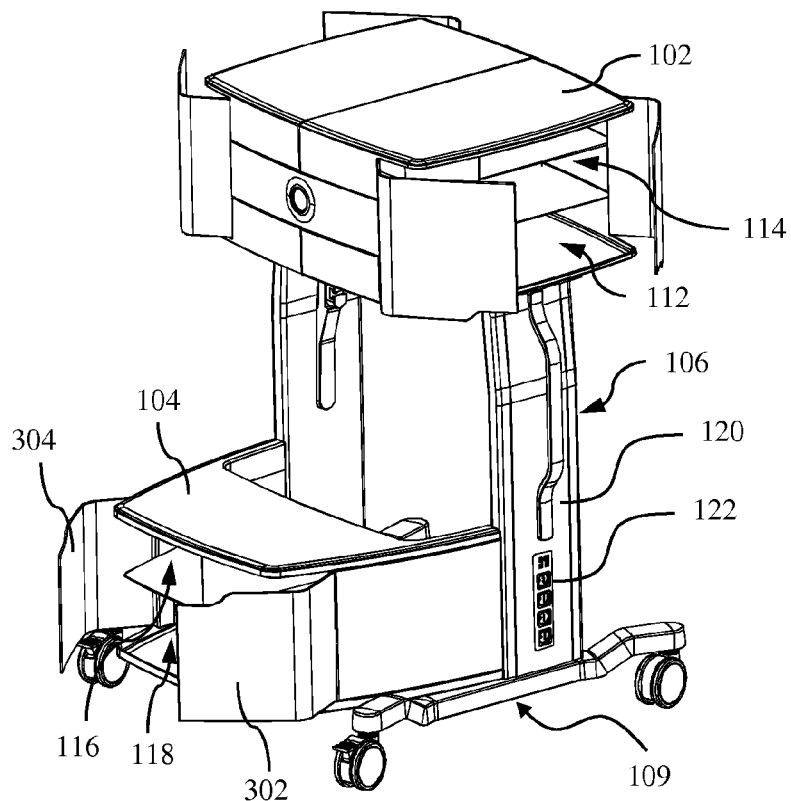
FIG. 3 is a schematic illustration of a device integration module of the integrated modular system with multiple compartments according to an embodiment.

Each device integration module includes one or more compartments such as a compartment 112 and a compartment 114 of the device integration module 102 as shown in FIG. 3. These compartments may be also modular as the compartment size and their configuration can be varied. In an embodiment the compartments may be formed by multiple walls or partitions. The walls may be of different configurations such as shape and dimensions. These walls can be arranged in different manner to form compartments of different size and configuration. Medical equipments may be placed within the device integration module 102 in compartments 112 and 114 as illustrated in FIG. 3. The medical equipment may be connected to each other using different cables. As the compartments are also modular different compartments can be formed and the medical equipment can be rearranged and placed in them. Moreover other medical equipment of different sizes can be also arranged within the device integration module 102.

Similarly the device integration module 104 may also include multiple compartments such as a compartment 116 and a compartment 118 as shown in FIG. 3. These compartments are also modular as the compartment size and their configuration can be varied. In an embodiment the compartments may be formed by multiple walls or partitions. The walls may be of different configurations such as shape and dimensions. These walls can be arranged in different manner to form compartments of different size and configuration. Medical equipment may be placed within the device integration module 104 in compartments 116 and 118. The medical equipment may be connected to each other using different cables. As the compartments are also modular different compartments can be formed and the medical equipment can be rearranged and placed within them. Moreover other medical equipment of different sizes can also be arranged within the device integration module 104. The device integration module 104 also includes access openings 302 and 304 that can be opened to access the compartments.

The medical equipment when placed in the device integration modules 102 and 104 needs to be connected to a power unit and/or connected to each other using multiple cables or wires. Referring back to FIG. 1, the wires or cables of the medical equipments passes through one or more cable raceway networks. For instance a holding structure 120 of the supporting structure 106 may have a hollow configuration that allows the wires and cables to pass through the structure and remain concealed. Thus the hollow configuration forms a cable raceway network. In this embodiment the wires and cables can be accessible by opening the holding structure 120. It may be envisioned that the cable raceway network may be an integral part of the supporting structure 106 or a separate part that may be disposed in the supporting structure 106 and also may have any other structural configuration for managing the wires or cables of the medical equipments in an efficient manner. When the medical equipment are arranged in the device integration modules 102 and 104 the wires and cables run through within the cable raceway networks in the supporting structure 106 and then gets connected to the medical device housed in the device integration modules. For instance a cable raceway network in the supporting structure 106 may enable navigation of one or more cables between the supporting structure 106 and the device integration module 102. Further another cable raceway network may enable navigation of the one or more cables between the supporting structure 106 and the device integration module 104. As the wires and cables are placed within the supporting structure 120 they can be managed efficiently and any disorder around the patient is avoided and further entangling of these wires and cables are also eliminated. Moreover as the wires and cables are not all over the place around the patient confusion does not arise in any manner for a medical expert managing the patient. The supporting structure 106 may also include a power supply unit 122 as illustrated in FIGS. 1 and 2. The integrated modular system 100 is configured to secure a plurality of medical devices while protecting them against any liquid ingress and providing adequate access to the user for their operation and monitoring as desired from time to time.

Figure 4:
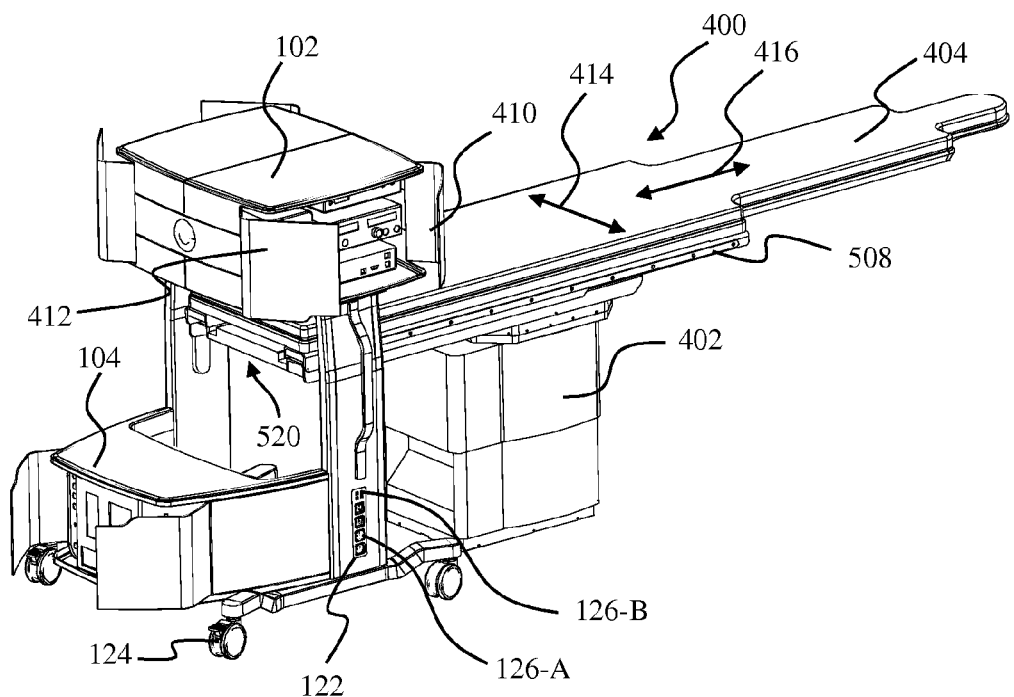
FIG. 4 is a schematic illustration of the device integration module of FIG. 3 having multiple medical devices integrated there within and also illustrates the integrated modular system for managing a plurality of medical device in an interventional procedure rooms as coupled to the tabletop of a patient positioner.
Figure 5:
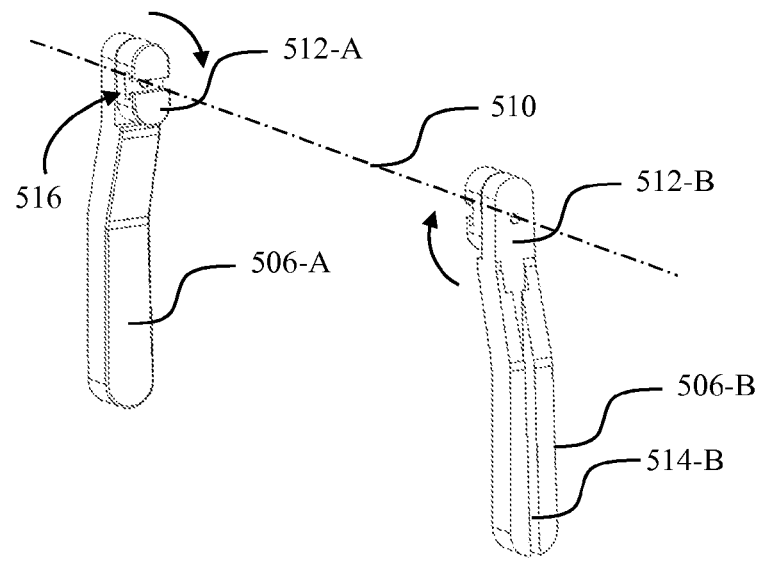
FIG. 5 is a schematic illustration of the coupling device having multiple degrees of freedom.
Figure 6:
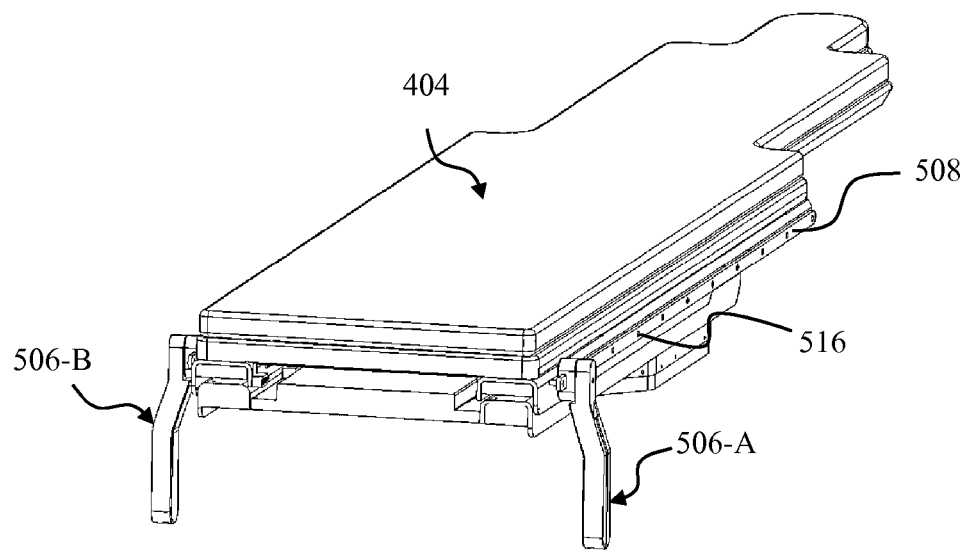
FIG. 6 illustrates the coupling device having multiple degrees of freedom in conjunction with the tabletop of a patient positioner

Now FIG. 4 illustrates a patient table management system 400 according to an embodiment. The patient table management system 400 includes a patient positioner 402 for carrying a patient. The integrated modular system 100 can be positioned with respect to the patient positioner 402 as shown in FIG. 4. The integrated modular system 100 is positioned at one end of the patient positioner 402. The patient positioner 402 may have an articulating table top 404 (hereinafter referred to as "table top 404"). When positioned the device integration module 102 and the device integration module 104 may be disposed towards mutually opposite directions with respect to the table top 404. The integrated modular system 100 is movable along the ground using multiple wheels such as a wheel 124-A and a wheel 124-B provided at the wheeled base 109. The wheels may be but not limited to spherical wheels and swiveling wheels. In an embodiment the integrated modular system 100 may include four wheels that facilitate its movement. The integrated modular system 100 is movable and may be connected to the patient positioner 402. In an embodiment multiple coupling devices (for instance coupling devices 506-A and 506-B, hereinafter collectively referred to as coupling devices 506) shown in FIG. 5 may be used to connect the integrated modular system 100 to the patient positioner 402. The tabletop 504 may have a rail 508 (shown in FIG. 6) for receiving the coupling devices 506 to ensure that the integrated modular system 100 is positioned with respect to the patient table top 404 without leading to any unintended relative movement. Thus the integrated modular system 100 can be moved away from the tabletop 404 only once the coupling devices 506 are disengaged from the tabletop 404. The coupling device (also may be a coupling device actuator) may be but not limited to a solenoid based electromechanical coupling, a mechanical coupling, an electromechanical coupling and so on. The coupling devices 506-A and 506-B may be arranged on the rails of the tabletop 404 as shown in FIG. 6. For instance the coupling device 506-A may be arranged on a rail 508. When arranged the coupling devices 506-A and 506-B are aligned with respect to an axial line 510. Each coupling device includes a pivot coupling block and a guide rail. For instance the coupling device 506-A includes a pivot coupling block 512-A and a guide rail 514-A and the coupling device 506-B includes a pivot coupling block 514-A (not shown in FIG. 6) and a guide rail 514-B. The pivot coupling blocks 512-A and 512-B may rotate with respect to the axial line 510 shown in FIG. 5. The pivot coupling block 512-A may have a guide way 516 that passes through the rail 508 of the tabletop 404. The rail 508 includes multiple slots such as a slot 518 that enables the pivot coupling block 512-A to be positioned at a particular location on the rail 508 upon engaging the guide way 516 with a slot. The guide rail in the coupling device can engage with the holding structure 120. The guide rail enables the device integration module 102 to move up and down with respect to the holding structure 120. For instance the coupling device 506-B with the help of the guide rail 514-B slidably moves with respect to the holding structure 120 in a vertical direction and simultaneously the coupling device 506-A have also a guide rail (not shown in FIG. 5 and FIG.

6) that enables it to move in a vertical direction. The coupling devices 506-A and 506-B facilitate movement of the device integration module 102 in a vertical orientation.

In an embodiment the height of the table top 404 can be adjusted to position the patient lying on the table top 404 at a desired height without disengaging the integrated modular system 100 from the table top 404. Here the coupling devices 506 and the supporting structure 106 enable the table top 404 to be raised and lowered without interfering with the device integration modules 102 and 104. The guide rails in the coupling devices 506 enable the table top 404 to be raised or lowered without disengaging the integrated modular system 100 from the table top 404. When the integrated modular system 100 is placed with respect to the patient positioner 502, an open region 520 (shown in FIG. 4) is present through which the table top 504 is positioned or engaged. The device integration module 102 may be at a higher position above the table top 404. Whereas the device integration module 104 may be at a lower position below the table top 404 as illustrated in FIG. 4. Further in an embodiment a coupling device may have a plurality of degrees of freedom. The coupling device may be pivotally secured or secured in a linearly guided fashion along the vertical direction with the supporting structure 106. Thus the coupling device enables the table top 404 to be oriented at multiple degrees of freedom with respect to the floor as may be needed for positioning the patient during the procedure. Thus the coupling devices 506 and the supporting structure 106 also enable the table top 404 to be tilted about a lateral axis with respect to the table top 404. For instance when the table top 404 is tilted at an angle with respect to the floor, the pivot coupling block 512-A rotates with respect to the axial line 510. The rotation of the pivot coupling block 512-A happens due to the engagement of the rail 508 with the guide way 516 of the pivot coupling block 512-A (explained earlier). So based on the orientation of the table top 404 the pivot coupling block 512-A and the pivot coupling block 512-B rotates to keep the device integration module 102 in an erect position or without disturbing its position. The coupling devices 506 and the support structure 106 enable the table top 504 also to be displaced in a lateral direction shown by an arrow 414 while simultaneously displacing the supporting structure 106 with the wheeled base 109 and the device integration module 102 in the same direction. Further the coupling devices 506 and the support structure 106 may also enable the table top 404 to be displaced in a longitudinal direction shown by an arrow 416 while simultaneously displacing the supporting structure 106 with the wheeled base 109 and the device integration module 102 in the same direction.

The device integration module 102 has doors 410 and 412 that can be opened to access the equipment placed within this segment. During the procedure the doors 410 and 412 may be partially or completely closed.

Figure 7:
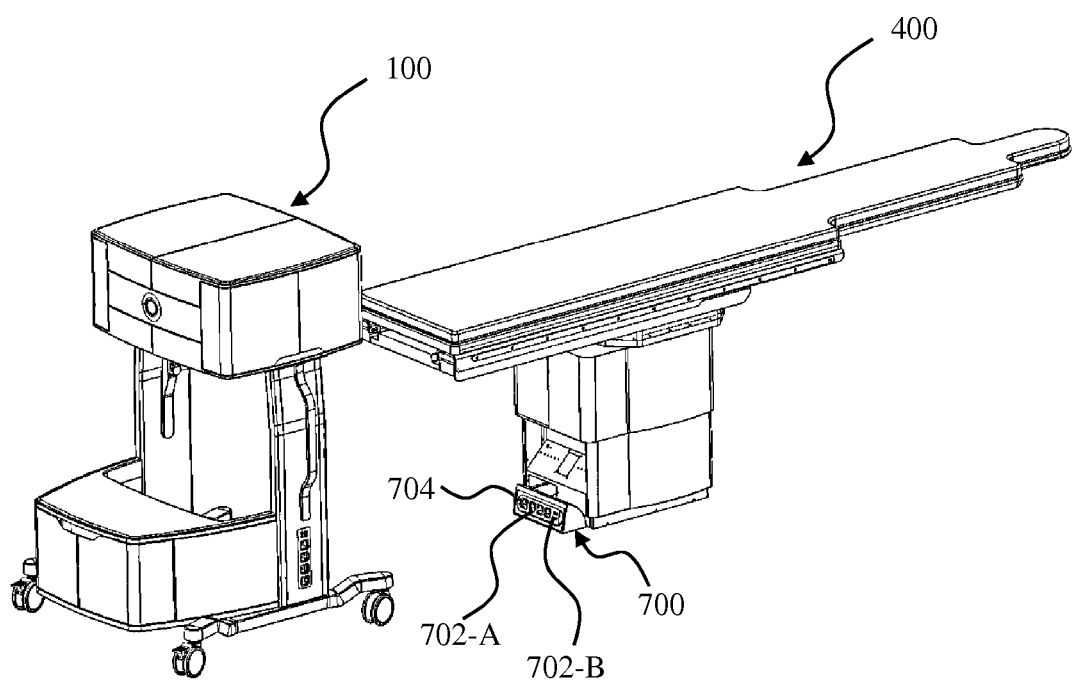
FIG. 7 illustrates a power supply and data connectivity unit disposed along the floor of the procedure room and disposed near the patient positioner there within and accessible to the user for establishing connections present in the integrated modular system 100.

Now moving on to FIG. 7, this illustrates a power supply and data connectivity unit 700 positioned along the floor of the procedure room and disposed near the patient positioner 602. The integrated modular system 100 may draw power supply and data connection from the power supply and data connectivity unit 700 using one power cable and one data cable (not shown in FIG. 7 for sake of convenience of representation). The power and data connection is then shared among multiple devices integrated into the integrated modular system 100 for instance using multiple other wires that may be arranged within the device integration module 102. The power supply and data connectivity unit 700 may be powered using an external power supply unit (not shown in FIG. 7). As a result entangling of wires and presence of wires along the floor is avoided. In another embodiment the power supply and data connectivity unit 700 receives power from an external power storage unit.

In this case the external power storage unit may include but not limited to a battery, a series of battery or a rechargeable battery or rechargeable batteries, and any type of energy storage units. The power supply and data connectivity unit 700 includes multiple power sockets such as power socket 702-A and data socket 702-B for connecting the medical equipment. The power socket 702-A and data socket 702-B are disposed at an external face of a socket plate 704. Similarly the power supply unit 122 also includes multiple power and data sockets such as a power socket 126-A and data socket 126-B as shown in FIG. 4. The power socket 126-A and data socket 126-B are disposed at an external face of a power supply unit 122 Further the integrated modular system 100 includes multiple wheels for example the wheel 124 that enables it move from one location to another.

Figure 8:
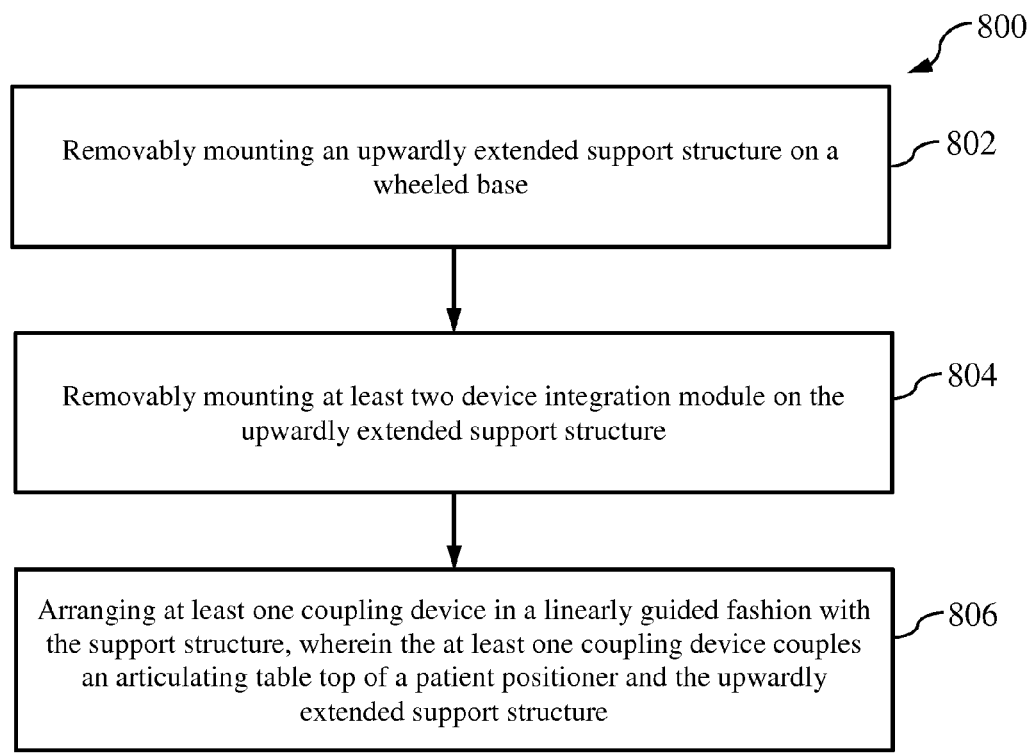
FIG. 8 illustrates a block diagram of a method 800 of assembling an integrated modular system for managing a plurality of medical devices according to an embodiment.

FIG. 8 illustrates a block diagram of a method 800 of assembling an integrated modular system for managing a plurality of medical devices according to an embodiment. The method 800 involves mounting a supporting structure on a wheeled base at block 802. The wheeled base may include multiple wheels for moving the integrated system to move around. The supporting structure may be upwardly extendible. Then at block 804 removably mounting one or more device integration modules on the support structure. The one or more device integration modules include a first device integration module and a second device integration module. The first device integration module and the second device integration module may be disposed towards mutually opposite direction with respect to the articulating table top of the patient positioner. Each device integration module may have space in the form of compartments for storing a plurality of medical devices. The device integration module also have access opening for accessing the medical devices. The integrated modular system can be aligned with respect to an articulating table top of a patient positioner. At block 806 one or more coupling devices are arranged in a linearly guided fashion with the supporting structure. The coupling devices can couple the articulating table top to the supporting structure. Now the integrated modular system can be placed at different positions with respect to the patient positioner. Further the articulating table top can be arranged at different angles and the supporting structure can be extended so that the device integration modules does not interfere the movement of the articulating table top.

The height of the integrated modular system can be adjusted to accommodate a patient lying on the patient positioner underneath the device integration module. Here the coupling devices and the supporting structure enable the table top to be raised and lowered without interfering with the device integration modules. More specifically the holding structures such as a holding structure can be extended to adjust the height of the integrated modular system. When the integrated modular system is placed with respect to the patient positioner, an open region is present through which the table top is placed. The first device integration module may be at a higher position above the table top. Whereas the second device integration module may be at a lower position below the table top. Further in an embodiment a coupling device may have a plurality of degrees of freedom. For instance the coupling device may be pivotally secured with the supporting structure. So if the table top is positioned in different orientation such as inclined at an angle to the ground then the coupling devices can be oriented such that it does not disturb the position of the device integration modules in the integrated modular system and accommodates the table top. The coupling devices and the supporting structure also enable the table top to be tilted about a lateral axis with respect to the ground.

The coupling devices and the support structure enable the table top also to be displaced in a lateral direction while simultaneously displacing the supporting structure with the wheeled base and the device integration module in the same direction. Further the coupling devices and the support structure may also enable the table top to be displaced in a longitudinal direction while simultaneously displacing the supporting structure with the wheeled base and the device integration module in the same direction.

Further one or more cable raceway networks are integrated within the supporting structure for arranging a plurality of cables of the medical devices in a concealed fashion. For instance a holding structure 120 of the supporting structure 106 may have a hollow configuration that allows the wires and cables to pass through the structure and remains concealed. Thus the hollow configuration forms a cable raceway network. In this embodiment the wires and cables can be accessible by opening the holding structure. It may be envisioned that the cable raceway network may be an integral part of the supporting structure or a separate part that may be disposed in the supporting structure and also may have any other structural configuration for managing the wires or cables of the medical equipment in an efficient manner. When the medical equipment are arranged in the device integration modules the wires and cables run through within the cable raceway networks in the supporting structure and then gets connected to the medical device housed in the device integration modules. For instance a cable raceway network in the supporting structure may enable navigation of one or more cables between the supporting structure and the device integration module. Further another cable raceway network may enable navigation of one or more cables between the supporting structure and the device integration module. As the wires and cables are placed within the supporting structure they can be managed efficiently and any disorder around the patient is avoided.

From the foregoing, it will be appreciated that the above integrated modular system for a healthcare environment provides numerous benefits to healthcare enterprises, such as improved way of managing medical equipment used in the healthcare environment such as operation theatre, and a medical diagnostic environment. Further as the integrated modular system is capable of freely moving in tandem with the tabletop of the patient table thereby eliminating any undesired pull or strain on the patient connected cables, tubes or catheters. The coupling device provided is configured to be simultaneously movable in rotational fashion about a horizontal axis and linear fashion in a vertical direction and configured to be firmly clamped onto the edge of the articulating tabletop of the patient table thereby facilitating the longitudinal, lateral, vertical, rotational or inclined movement of tabletop. As a result free movement of integrated modular system is achievable in tandem with tabletop. The integrated modular system facilitates plurality of medical devices to be interconnected among themselves and interacting with patient and external devices and configured to route all interconnecting cables including power, signal and data cables as well as tubing for gases, liquids and catheters in an orderly fashion eliminating all unnecessary exposed cables and tubing.

This written description uses examples to disclose the invention, including the best mode, and also to enable any person skilled in the art to practice the invention, including making and using any computing system or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

We claim:

1. An integrated modular system for managing a plurality of medical devices, the integrated modular system comprising:
    a wheeled base;
    an upwardly extended supporting structure mounted on the wheeled base;
    an at least two device integration module removably mounted on the upwardly extended supporting structure and comprising a first device integration module and a second device integration module; and
    at least one coupling device arranged in a linearly guided fashion with the upwardly extended supporting structure,
    wherein the at least one coupling device couples an articulating table top of a patient positioner and the upwardly extended supporting structure and enables the articulating tabletop of the patient positioner to be coupled with the upwardly extended supporting structure when the patient positioner is moved in a longitudinal direction.

2. The integrated modular system of claim 1, wherein the at least one coupling device and the upwardly extended supporting structure further enables the articulating tabletop of the patient positioner to be at least one of:
    raised and lowered without interfering with at least one of the at least two device integration module;
    displaced in a lateral direction while simultaneously displacing the upwardly extended supporting structure along with the wheeled base and the first device integration module in same direction; and
    displaced in a longitudinal direction while simultaneously displacing the upwardly extended supporting structure along with the wheeled base and the first device integration module in the same direction.

3. The integrated modular system of claim 1, wherein at least one of the at least two device integration module is configured to house a plurality of medical devices, wherein each of the at least two device integration module comprises at least one access opening to provide user access to the plurality of medical devices and manage cables of the plurality of medical devices.

4. The integrated modular system of claim 1, wherein the first device integration module and the second device integration module are disposed towards mutually opposite directions with respect to the articulating tabletop of the patient positioner.

5. The integrated modular system of claim 1, wherein the wheeled base comprises a plurality of wheels comprising one of spherical wheels and swiveling wheels.

6. An integrated modular system for managing a plurality of medical devices, the integrated modular system comprising:
    a wheeled base;
    an upwardly extended supporting structure mounted on the wheeled base;

an at least two device integration module removably mounted on the upwardly extended supporting structure and comprising a first device integration module and a second device integration module; and at least one coupling device arranged in a linearly guided fashion with the upwardly extended supporting structure, wherein the at least one coupling device couples an articulating table top of a patient positioner and the upwardly extended supporting structure, and is secured in a pivoted fashion with the upwardly extended supporting structure.

7. The integrated modular system of claim 6, wherein the coupling device and the upwardly extended supporting structure enable the articulating tabletop of a patient positioner to be tilted about a lateral axis.

8. An integrated modular system for managing a plurality of medical devices, the integrated modular system comprising:
a wheeled base;
an upwardly extended supporting structure mounted on the wheeled base;
an at least two device integration module removably mounted on the upwardly extended supporting structure and comprising a first device integration module and a second device integration module;
at least one coupling device arranged in a linearly guided fashion with the upwardly extended supporting structure, wherein the at least one coupling device couples an articulating table top of a patient positioner and the upwardly extended supporting structure; and
at least one cable raceway network integrated within the upwardly extended supporting structure and configured to arrange a plurality of cables in a concealed fashion.

9. The integrated modular system of claim 8, wherein a cable raceway network of the at least one cable raceway network enables navigation of at least one cable of the plurality of cables between the upwardly extended supporting structure and the first device integration module.

10. The integrated modular system of claim 8, wherein a cable raceway network of the at least one cable raceway network enables navigation of at least one cable of the plurality of cables between the upwardly extended supporting structure and the second device integration module.

11. The integrated modular system of claim 8, wherein the plurality of cables comprises electrical power cables, data cables and pneumatic tubing.

12. The integrated modular system of claim 8, wherein a cable raceway network of the at least one cable raceway network comprises a socket plate and at least one socket disposed at the external face of the socket plate and accessible to the user for establishing connection of the plurality of cables, wherein the at least one socket comprises an electrical socket, a data port and a pneumatic port.

13. The integrated modular system of claim 12, wherein each cable raceway network of the plurality of cable raceway networks is configured to have an access opening along at least one section of its length to lay the plurality of cables inside the each cable raceway network and a cover plate to access the plurality of cables.

14. An integrated modular system for managing a plurality of medical devices, the integrated modular system comprising:
a wheeled base;
an upwardly extended supporting structure mounted on the wheeled base;
an at least two device integration module removably mounted on the upwardly extended supporting structure and comprising a first device integration module and a second device integration module; and
at least one coupling device arranged in a linearly guided fashion with the upwardly extended supporting structure,
wherein the at least one coupling device couples an articulating table top of a patient positioner and the upwardly extended supporting structure, and each of the at least two device integration module comprise at least one common bus configured for establishing shared connectivity between the plurality of devices housed inside the at least two device integration module.

15. The integrated modular system of claim 14, wherein the at least one common bus serves to provide connectivity to power, data or pneumatic resources.

16. A method of assembling an integrated modular system for managing a plurality of medical devices, the method comprising:
removably mounting an upwardly extended supporting structure on a wheeled base; removably mounting an at least two device integration module comprising a first device integration module and a second device integration module on the upwardly extended supporting structure;
arranging at least one coupling device in a linearly guided fashion with the supporting structure, wherein the at least one coupling device couples an articulating table top of a patient positioner and the upwardly extended supporting structure; and
integrating at least one cable raceway network within the upwardly extended supporting structure and configured to arrange a plurality of cables in a concealed fashion.

17. The method of claim 16, wherein the at least one coupling device and the upwardly extended supporting structure enable the articulating tabletop of the patient positioner to be at least one of:
raised and lowered without interfering with at least one of the at least two device integration module;
displaced in a lateral direction while simultaneously displacing the upwardly extended supporting structure along with the wheeled base and the first device integration module in same direction; and
displaced in a longitudinal direction while simultaneously displacing the upwardly extended supporting structure along with the wheeled base and the first device integration module in the same direction.

18. The method of claim 16 further comprising disposing the first device integration module and the second device integration module towards mutually opposite directions with respect to the articulating tabletop of the patient positioner.

19. The method of claim 16, wherein a cable raceway network of the at least one cable raceway network enables navigation of at least one cable of the plurality of cables between the upwardly extended supporting structure and one of the first device integration module and the second device integration module.

20. The method of claim 16 further comprising arranging a plurality of medical devices in the at least two device integration modules, wherein each of the at least two device integration modules comprises at least one access opening to provide user access to the plurality of medical devices and manage cables of the plurality of medical devices.

* * * * *